(12) United States Patent
Benjauthrit et al.

(10) Patent No.: US 8,642,325 B1
(45) Date of Patent: Feb. 4, 2014

(54) ADVANCED PHOTOBIOREACTOR DEEP POND SYSTEM

(76) Inventors: Saranya Benjauthrit, La Canada, CA (US); Jean Benjauthrit, La Canada, CA (US); Boonsieng Benjauthrit, La Canada, CA (US)

( * ) Notice: Subject to any disclaimer, the term of this patent is extended or adjusted under 35 U.S.C. 154(b) by 814 days.

(21) Appl. No.: 12/690,512

(22) Filed: Jan. 20, 2010

Related U.S. Application Data (60) Provisional application No. 61/145,970, filed on Jan. 21, 2009, provisional application No. 61/171,416, filed on Apr. 21, 2009.

(51) Int. Cl.
 *C12M 1/00* (2006.01)
 *C12M 3/00* (2006.01)
 *C12N 1/12* (2006.01)
(52) U.S. Cl.
 USPC .......... 435/292.1; 435/257.1; 435/289.1; 435/946
(58) Field of Classification Search
 None
 See application file for complete search history.

(56) References Cited

U.S. PATENT DOCUMENTS

| | | | | | |
|---|---|---|---|---|---|
| 4,657,677 | A | * | 4/1987 | Roubicek et al. | 210/219 |
| 6,192,833 | B1 | * | 2/2001 | Brune et al. | 119/204 |
| 7,198,940 | B2 | * | 4/2007 | Vellinger et al. | 435/286.5 |
| 2008/0311649 | A1 | * | 12/2008 | Cloud et al. | 435/292.1 |

* cited by examiner

*Primary Examiner* — Debbie K Ware
(74) *Attorney, Agent, or Firm* — Michael D. Eisenberg (57) ABSTRACT

An apparatus for cultivating algae integrates a deep pond approach with an advanced photobioreactor concept. The apparatus comprises a deep (one foot or deeper) pond with a v-shaped or trough bottom, where, through gravity, algae will settle to the bottom of the trough and be pumped through a clear pipe located near or submerged under the surface of aqueous algae fluid via a heating pipe, which is also located near the surface of the algae fluid and be sprayed out into the air through spraying pipes distributed throughout the pond. With the combination of a v-shaped bottom deep pond, gravity, and clear pipes under aqueous algae fluids, algae can be exposed to sunlight much longer than the conventional approaches without being over exposed or heated and can thereby provide substantially better yields. The invention also introduces an electro-mechanical scrubbing ball that can be used to clean the piping system remotely.

20 Claims, 9 Drawing Sheets

ADVANCED PHOTOBIOREACTOR DEEP POND SYSTEM

CROSS-REFERENCES TO RELATED APPLICATIONS

This application claims priority from U.S. Provisional Application Ser. No. 61/145,970 filed Jan. 20, 2009, and U.S. Provisional Application Ser. No. 61/171,416 filed Apr. 21, 2009 which are hereby incorporated herein by reference in the respective entirety of each.

TECHNICAL FIELD

The present invention relates to microorganism cultivation and production systems, and more particularly, some embodiments relate to advanced photobioreactor and deep pond systems for algae cultivation.

BACKGROUND OF THE INVENTION

In order to improve living quality, humanity has invented numerous apparatuses such as automobiles, trains, airplanes, and other machineries. These machineries require fuels to operate and due to their vast abundance, fossil fuels such as petroleum oil and coal have been used. One unfortunate characteristic about fossil fuels is that their end products are pollutants, such as $CO_2$ and carbon particulates, that have been found to affect living quality and the world's climate, known as the green house effect. With the rapid increase in the world's population, these natural resources have been found to deplete at a very rapid rate while their side effects have caused a great concern to humanity on both their health and living environment. This has motivated searches for renewable energy sources that can help to solve these problems. Oils from animals and plants have been found to ameliorate these problems to some extent and have been employed ever since. However, to meet the world demands for renewable energy, oils from animals and plants alone will be insufficient. For example, to meet the projected world's energy demands for biofuels by 2100 (351 ExaJoules/year), the entire agricultural land (about 1.5 billion hectares), will be needed (Huesmann, 2006). In the U.S. alone, it would take all 190 million-hectares of crop land (Kheshgi et al 2000) to produce ethanol from corn to replenish the gasoline need, which amounts to about 25% of the energy demand. This clearly indicates that other alternative sources for producing biofuels are in dire need. Due to their rapid growth (in hours rather than days or months) with minimal food and maintenance supports, algae, both macro and micro, appear to be the choice. During the energy crisis of the 1970s, the Aquatic Species Program (ASP) of the Department of Energy has identified 3000 species out of about 100,000 known algae species for development and they have finally narrowed them down to 300 species, both fresh and salt water varieties, for further works on oil producing capabilities.

Microalgae (or, for convenience, algae) are unicellular organisms that can grow very rapidly by photosynthesis using waste products and $CO_2$. Besides using as a renewable biomass source for diesel fuel substitute (generally called biodiesel) and other biofuels such as methane, ethanol, and hydrogen, algae are also used as a source of proteins, fatty acids, and other biochemicals in food products as well as animal feed supplements. Further, they are used in the production of oxygen, vitamins, minerals, pharmaceuticals, and natural dyes. Gases released from fossil fuel production and utilization such as $CO_2$, $NO_x$, $VO_x$ can all be effectively scrubbed by algae, while nitrogen, phosphorous, and toxic substances in sewage treatment can also be removed by algae. Other applications of algae include biological control of agricultural pests and biodegradation of plastics. As a by-product, they are used as soil conditioners and biofertilizers in farming. This clearly indicates that a mass production of algae at low cost with high yield would be of great desire.

Two major advantages have been found in microalgae over other terrestrial plants such as soybeans, corn, jutropha, or palm. First, algae have a much higher growth rate and consequently their biomass productivities over space and time are significantly greater. Based on ash-free dry weight (AFDW, e.g., organic matter), the current algal yield is around 70 metric tons per hectare per year (mt/ha/yr), while the yields of soybeans, corn, and switchgrass or hybrid poplars are only 3, 9, 10-13 mt/ha/yr, respectively; accordingly, the footprint of biofuel systems in terms of both land and water is much smaller. Second, algae are more tolerant to varying environmental conditions. They can grow on non-arable land, using saline or brackish water. Many species of algae, such as *Dunaliella*, grow in seawater and can use $CO_2$ from desulphurized flue gases of fossil-fuel fired power plants. Also, culturing algae in aqueous fluid instead of soil promotes their access to resources such as water, $CO_2$, and minerals. For these reasons, about one-third of the net photosynthetic activity in the world is from algae. The combination of high biomass productivities, and the lack of needs for arable land and freshwater will enable the large-scale production of biofuels without disturbing food crops, and agricultural and forest land, while restoring the Earth from global warming problems.

Published oil yields of various species are: *Chlorella minuttssima* 31% (Illman et al., 2000); *Isochrysis galbana* 39% (Fidalgo et al., 1998); *Nannochloropsis* sp. 38% (Fábregas et al., 2004); and *Tetraselmis suecica* 30% (Otero and Fábregas, 1997). Some other algae such as *Botryococcus bruinii* have been found to yield as much as 75-80% of their dry weight.

The traditional practice in growing microalgae is to use a shallow raceway pond (Oswald 1960). This type of pond comprises of a curved-edge oblong rectangular pond with a middle island dividing the pond into two separate raceways. The pond is typically 20-30 cm deep and is driven by a large paddlewheel installed on one corner of the pond. The idea of being shallow is to allow maximum exposure of microalgae to sunlight. The idea of a paddlewheel is to keep microalgae agitated so it will be constantly exposed to sunlight. Unfortunately, neither of these ideas appears to be effective. With the pond being shallow, only small amount of microalgae can be grown in a fairly large area. With a large paddlewheel driving a large amount of fluid is neither economic nor effective. Most of microalgae would start to settle down toward the bottom of the pond as soon as it propelled away from the paddlewheel. From a calculation, most microalgae have an average of exposure time of only 3 minutes for an eight-hour of pond sun exposure. Attempts to improve yields and productivities of raceway ponds have been document in U.S. Pat. Nos. 6,192,833 on a partitioned aquaculture system and 7,198,940 on a controlled eutrophication process. These patents provide value-added applications to the raceway pond concept by augmenting them with a fish pond and a controlled eutrophication process with the basic weaknesses still remain.

Another pond design that has been considered is the deep-pond concept. This concept has not been generally accepted due to the fact that microalgae will most of the time (70%)

remain in the dark region where sunlight cannot reach, which will consequently result in less growth.

To overcome both dilemmas discussed above, the concept of photobioreactor has been conceived and implemented. This concept attempts to provide sunlight exposure of microalgae by channeling microalgae fluid through a clear polyethylene tubing or pipe that is constantly exposed to sunlight through various configurations: vertical, sloped, horizontal, etc. (U.S. Pat. No. 5,162,051 and a review article by Yuan-Kim Lee on "Enclosed Bioreactors for the Mass Cultivation of Photosynthetic Microorganisms: The Future Trend", TIBTECH, July 1986, pgs. 186-189). The concept, again, is also unfortunate, which often results in sunlight saturation, inhibition, and respiration, especially during high sunlight period of the day. High sunlight in a relatively short light path length (tube) can damage and/or kill algae cells. There have been several techniques in overcoming sunlight over exposure such as using cover shielding during peak hours, placing these tubular structures inside a green house, etc. Examples of recent attempts to improve the concept have been documented in U.S. patent application No. 60/932,674, filed May 31, 2007 and provisional application no. 20080311649. Again, these applications deal mainly with logistics and controls of the design in attempts to improve yields, but the basic concepts are still essentially the same. These techniques have worked to some extent, but either way, the concept of photobioreactors is basically rather costly and volume limited, which is often a major factor in large-scale commercial production. On large-scale production, photobioreactors will not only be too costly, but it is almost impossible to implement, even in a hybrid system that combines the concept of raceway pond with a photobioreactor. For example, on a very large raceway pond of, say, 4 acre-feet or pond of size 656'×164'×1.64'—176438 cuft or 1,376,215 gallons of microalgal fluid—it would take 95-143 days to circulate the microalgae fluid at 20-30 cm/sec using a 2"-diameter clear pipe. In order to achieve one complete cycle in a day, the flow rate of the fluid must be at least 13,759 gallons/minute for this 2"-diameter pipe, which will allow sunlight exposure of microalgae about only 0.1 minute/8 hour operation time. These numbers indicate impracticality of the system. The system will not only be rather expensive to implement, but its implementation may not work as well as it should be. The high flow rate may also cause damage to microalgal cells or it may deter proper growth of most microalgae.

The overall photosynthetic efficiency can be affected by many other factors for both existing raceway pond and photobioreactor approaches. These include the limited wavelength range of sunlight capable of driving photosynthesis (400-700 nm, which is being only 45% of the total solar energy), respiration requirements (during dark periods), efficiency of absorbing sunlight, and other growth conditions. So the need exists for a large-scale production system that can help to improve these efficiencies.

BRIEF SUMMARY OF EMBODIMENTS OF THE INVENTION

According to one embodiment of the invention, an advanced photobioreactor (APBR) deep pond for use to effectively cultivate algae comprises at least one circulation pump and at least one sucking pipe. One end of the pipe is capped off with a perforated cap and the other end is connected to a pump. A plurality of heating pipes for warming up aqueous algae fluids are provided, wherein an end of the pipes are connected to a pump and another end is connected to a clear pipe. A plurality of clear pipes are provided for exposing aqueous algae fluids to sunlight, wherein one end of the pipe is connected to a heating pipe and another other end is connected to a perforated or protruded spraying pipe. A plurality of perforated or protruded spraying pipes are provided for spraying aqueous algae fluids into the air, wherein both ends are capped off. The pump is used to pump (circulate) aqueous algae fluids from the sucking pipe into a clear pipe through the heating pipe and spray the aqueous algae fluids out into the air via a plurality of perforated or protruded spraying pipes. A plurality of heating rods for warming up aqueous algae fluids is provided. A second plurality of heating pipes for warming up aqueous algae fluids are provided. The second heating pipes are disposed around sides of the pond above ground. A second pump or plurality of pumps for circulating aqueous algae fluids is provided. A plurality of pipes for warming up aqueous algae fluids is provided. A plurality of pipes for circulating hot water in order to warm up aqueous algae fluids is provided. A deep pond is provided within which or above which all of the above items are located.

In a variant, the APBR deep pond has a depth of one foot or deeper has one or more v-shaped troughs in the bottom of the pond.

In another variant of the APBR deep pond, the sucking pipes are located at the bottom of each trough.

In a further variant of the APBR deep pond, the sucking pipes are perforated with holes and/or protruded with pipes of various lengths.

In still another variant of the APBR deep pond, the heating pipes are located adjacent a top surface of the aqueous algae fluids but not touching the surface, by being disposed on floats.

In yet a further variant of the APBR deep pond, the circulation pump is connected on the inlet to the sucking pipe via a vertical pipe and is connected on the outlet to the heating pipe.

In another variant of the APBR deep pond, the clear pipes are substantially translucent to sunlight and inhibit the transmission of UV light.

In still a further variant of the APBR deep pond, the clear pipes are submerged on the surface of the aqueous algae fluids with a top of the clear pipe aligned even with or below the surface of the aqueous algae fluids.

In yet another variant of the APBR deep pond, a gas relief valve is located above and beyond the surface of the aqueous algae fluids, and is connected to the clear pipe.

In another variant of the APBR deep pond, a $CO_2$ or Flue Gas Desulphurization (FGD) $CO_2$ injector is connected to the clear pipe.

In a further variant of the APBR deep pond, the $CO_2$ or FGD $CO_2$ injector is a venturi-type injector.

In yet another variant of the APBR deep pond, the $CO_2$ or FGD $CO_2$ injector is located above the surface of the aqueous algae fluids with a pipe extending down into the aqueous algae fluid down the bottom of the deep pond.

In still a further variant of the APBR deep pond, the heating rods are located at the bottom of the deep pond and above the surface of the trough and run parallel with the sucking pipe.

In another variant of the APBR deep pond, the circulation pipes of the hot water draw the hot water from geothermal wells and the hot water pipes are located at the side and/or bottom of the pond.

In a further variant, a method of cultivating algae, comprises: growing a species of algae in the APBR deep pond described above.

In another variant, the APBR deep pond comprises a remotely controlled electro-mechanical scrubbing (RCEMS) ball for cleaning pipes.

In still a further variant, the RCEMS ball comprises: an armature having first and second ends; a remote control and a rubberized ball, which contains a rechargeable battery pack; an electromechanical switch that can be turned on and off remotely; and an electric motor with both ends of the armature exposed outside, but sealed, with a round brush attached on each end.

In yet another variant of the APBR deep pond, a pocket is disposed at the ends of any of the one or more pipes configured to house the RCEMS ball during the non-operative period.

In a further variant, an advanced photobioreactor (APBR) deep pond system for use to effectively cultivate algae comprises: a seedling station for conditioning the aqueous fluids to be cultivated; a harvesting station for receiving the aqueous fluids being cultivated, and an advanced photobioreactor (APBR) deep pond for use to cultivate microalgae, where the APBR deep pond comprises: one or more perforated or protruded sucking pipes, wherein one end of the pipe is capped off with a perforated cap and the other end is connected to an electric pump; a plurality of heating pipes for use to warm up aqueous algae fluids, wherein one end is connected to a pump and the other end is connected to a clear pipe; a plurality of clear pipes for exposing aqueous algae fluids to sunlight, wherein one end of the pipe is connected to a heating pipe and the other end is connected to a perforated or protruded spraying pipe; a plurality of perforated or protruded spraying pipes for use to spray aqueous algae fluids into the air, wherein both ends are capped off; one or more electric pumps for pumping (circulating) aqueous algae fluids from the sucking pipe into a clear pipe through the heating pipe and spraying the aqueous algae fluids out into the air via a plurality of perforated or protruded spraying pipes; a plurality of heating rods for use to warm up aqueous algae fluids; a second plurality of heating pipes for use to warm up aqueous algae fluids to be located on supporting brackets situated around sides of the pond above ground; one or more second pumps for circulating aqueous algae fluids; a plurality of pipes for use to warm up aqueous algae fluids; a plurality of pipes for circulating hot water from geothermal wells in order to warm up aqueous algae fluids; and a liner covered deep pond within which or above which all of the above items are located.

In another variant, a method of cultivating algae comprises cultivating the algae in the APBR deep pond described above.

There is still an imperative need for an apparatus and method that can be used to cultivate microalgae for large-scale operation in a continuous and cost effective manner.

In one aspect, the present invention provides an advanced photobioreactor (APBR) deep pond for use to cultivate microalgae, where the APBR deep pond comprises a deep (one foot or deeper) pond with a trough bottom, where the distributed microalgae from the top of the pond will, in time, settle down by gravity, wherein a perforated pipe located at the bottom of the trough is used to suck these microalgae and piped up to the top to empty into a black heating pipe for a certain length for warm up the microalgae and then passed through a clear pipe, also located on the top, for another certain length before the microalgae fluid is sprayed out through a plurality of perforated pipes, above which there is a plurality of heating pipes connected to pipes submerged under the fluid in the pond for used to warm up the aqueous fluid through out the day when the weather is warm and shut off when the weather is cool, wherein there is a plurality of heating rods located through out the bottom part of the pond for use to provide heat during cold periods, above which there is a plurality of heating pipes or pads, where the fluid from the pond is circulated around in order to warm up through out the day for the purpose of keeping the temperature down during the night.

In one embodiment, in the APBR deep pond, there is a thick vinyl liner covered the surface of the pond in order to prevent aqueous algae fluid from being absorbed into the ground and at the same time to prevent silt dirt to mix into the aqueous algae fluid. The liner is fabricated from material selected from the group consisting of polyethylene, PVC, or other plastic composite.

In another embodiment, in the APBR deep pond, the trough bottom runs along the length of the pond. In this case, the slant of the trough is long with small slope. In still another embodiment, in the APBR deep pond, the trough bottoms run along both the width as well as the length of the pond, a diamond shaped bottom. In both cases, there are perforated pipes running along the bottom of the trough for use to suck up algae and reroute them to the top of the pond. Still in another embodiment, there are dual troughs that run along the width of the APBR deep pond with perforated pipes run along the bottom of each trough for use to suck algae up for distribution on the top as mentioned above. Still in another embodiment, in the APBR deep pond, there are multiple-trough bottoms with perforated pipes running at the bottom of each trough.

In another embodiment, in the APBR deep pond, the heating pipes are constructed from a plurality of black ABS pipes, copper pipes, or other good heat absorbing pipes.

In still another embodiment, in the APBR deep pond, the clear pipes are constructed from a plurality of polyethylene pipes, PVC pipes, or other clear plastic heat tolerant, UV-inhibit pipes. In another embodiment, in the APBR deep pond, the clear pipes are located at the level of aqueous algae fluid surface. In another embodiment, in the APBR deep pond, the clear pipes are located in a deeper region.

In another embodiment, in the APBR deep pond, the perforated pipes for spraying microalgae into the air are white PVC pipes, ABS black pipes, or other perforated pipes.

In another embodiment, in the APBR deep pond, the plurality of heating pipes are constructed from black ABS pipes, copper pipes, or other good heat absorbing pipes.

In another embodiment, in the APBR deep pond, the plurality of black pipes embedded a few feet under the ground connected to the perforated black pipes installed at the center of the trough. These pipes use the constant temperature of ground around 57.sup.o F to help to maintain a proper temperature for microalgae during hot or cold periods.

In another aspect, the present invention provides an APBR deep pond system for cultivating microalgae, where the system comprises a pre-treatment unit for conditioning the aqueous algae fluids to be cultivated; a post-treatment unit for receiving the aqueous algae fluids being cultivated, and an advanced photobioreactor (APBR) deep pond for use to cultivate microalgae, where the APBR deep pond comprises a deep (one foot or deeper) pond with a trough bottom, where the distributed microalgae from the top of the pond will, in time, settle down by gravity, wherein a perforated pipe located at the bottom of the trough is used to suck these microalgae and piped up to the top to empty into a black heating pipe for a certain length for warm up the microalgae and then passed through a clear pipe, also located on the top, for another certain length before the microalgae fluid is sprayed out through a plurality of perforated pipes, above which there is a plurality of heating pipes connected to pipes submerged under the fluid in the pond for used to warm up the aqueous algae fluid through out the day when the weather is warm and shut off when the weather is cool, wherein there are a plurality of heating rods located through out the bottom part of the pond for use to provide heat during cold periods, above which there is a plurality of heating pipes or pads, where the fluid from the pond is circulated around in order to warm up through out the day for the purpose of keeping the temperature up during the night.

In yet another aspect, the present invention provides a process for cultivating microalgae using the APBR deep pond and system provided herein.

Other features and aspects of the invention will become apparent from the following detailed description, taken in conjunction with the accompanying drawings, which illustrate, by way of example, the features in accordance with embodiments of the invention. The summary is not intended to limit the scope of the invention, which is defined solely by the claims attached hereto.

BRIEF DESCRIPTION OF THE DRAWINGS

The present invention, in accordance with one or more various embodiments, is described in detail with reference to the following figures. The drawings are provided for purposes of illustration only and merely depict typical or example embodiments of the invention. These drawings are provided to facilitate the reader's understanding of the invention and shall not be considered limiting of the breadth, scope, or applicability of the invention. It should be noted that for clarity and ease of illustration these drawings are not necessarily made to scale.

Some of the figures included herein illustrate various embodiments of the invention from different viewing angles. Although the accompanying descriptive text may refer to such views as "top," "bottom" or "side" views, such references are merely descriptive and do not imply or require that the invention be implemented or used in a particular spatial orientation unless explicitly stated otherwise.

FIG. 3b is a cross section taken along the line 3b'-3b' in FIG. 3a;

The figures are not intended to be exhaustive or to limit the invention to the precise form disclosed. It should be understood that the invention can be practiced with modification and alteration, and that the invention be limited only by the claims and the equivalents thereof.

DETAILED DESCRIPTION OF THE EMBODIMENTS OF THE INVENTION

From time-to-time, the present invention is described herein in terms of example environments. Description in terms of these environments is provided to allow the various features and embodiments of the invention to be portrayed in the context of an exemplary application. After reading this description, it will become apparent to one of ordinary skill in the art how the invention can be implemented in different and alternative environments.

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in applications, published applications and other publications that are herein incorporated by reference, the definition set forth in this document prevails over the definition that is incorporated herein by reference.

The present invention may be understood more readily by reference to the following detailed description of certain embodiments of the invention.

While the description will relate to many specific elements and techniques in order to better illustrate the principles of the present invention, it is to be appreciated that the present invention is not limited to the specific descriptions. The present invention can be practiced with variations to any specific elements and techniques without departing from the principles of the present invention. At the same time, many details and specifics that their omissions will not affect the practices of the present invention will be omitted from the description in order not to obscure the principles of the present invention.

Figure 1:
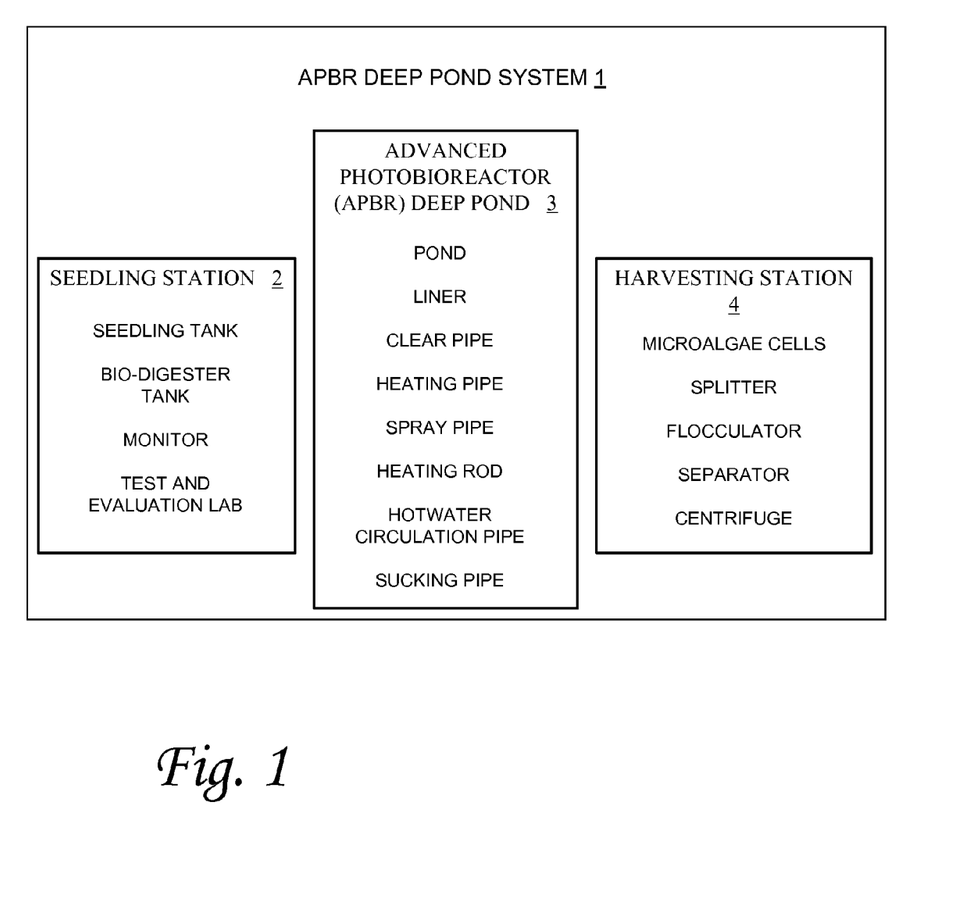
FIG. 1 is a block diagram illustrating the APBR deep pond system in accordance with one embodiment of the present invention.

Now referring to FIG. 1, there is provided an advanced photobioreactor (APBR) deep pond system 1 in accordance with one embodiments of the present invention. The APBR deep pond system 1 comprises a seedling station 2, an APRB deep pond 3, and a harvesting station 4. The seedling station 2 includes at least one tank of one type of microalgae seedling and an automatic pump for inoculating seedlings into the APBR deep pond, and a bio-digester tank for preparing food for the microalgae. The system 1 also includes various fertilizers and other accessories for cultivating microalgae. A small monitoring and test laboratory may also be included in this seedling station. The APBR deep pond 3 cultivates and nurtures the microalgae seedlings until they are ready for harvesting. The pond and its operation will be detailed hereinafter.

The harvesting station 4 carries out a harvesting process, which includes microalgae cells splitting; flocculation; oil, livestock feed supplement (LFS), water separation; and waste water treatment so water can be returned to the system for reuse. There are various known systems and processes that can be implemented to provide advantages, efficiencies, and better yields in the seedling station as well as in the harvesting station.

In a variant of the present invention, there is provided an APBR deep pond comprising a plurality of marine life such as fish, shrimp, shells, turtles, and the like, where microalgae in the pond serve as food for the marine life and at the same time the excretes of these marine lives serve as a food source for the microalgae.

Figure 2A:
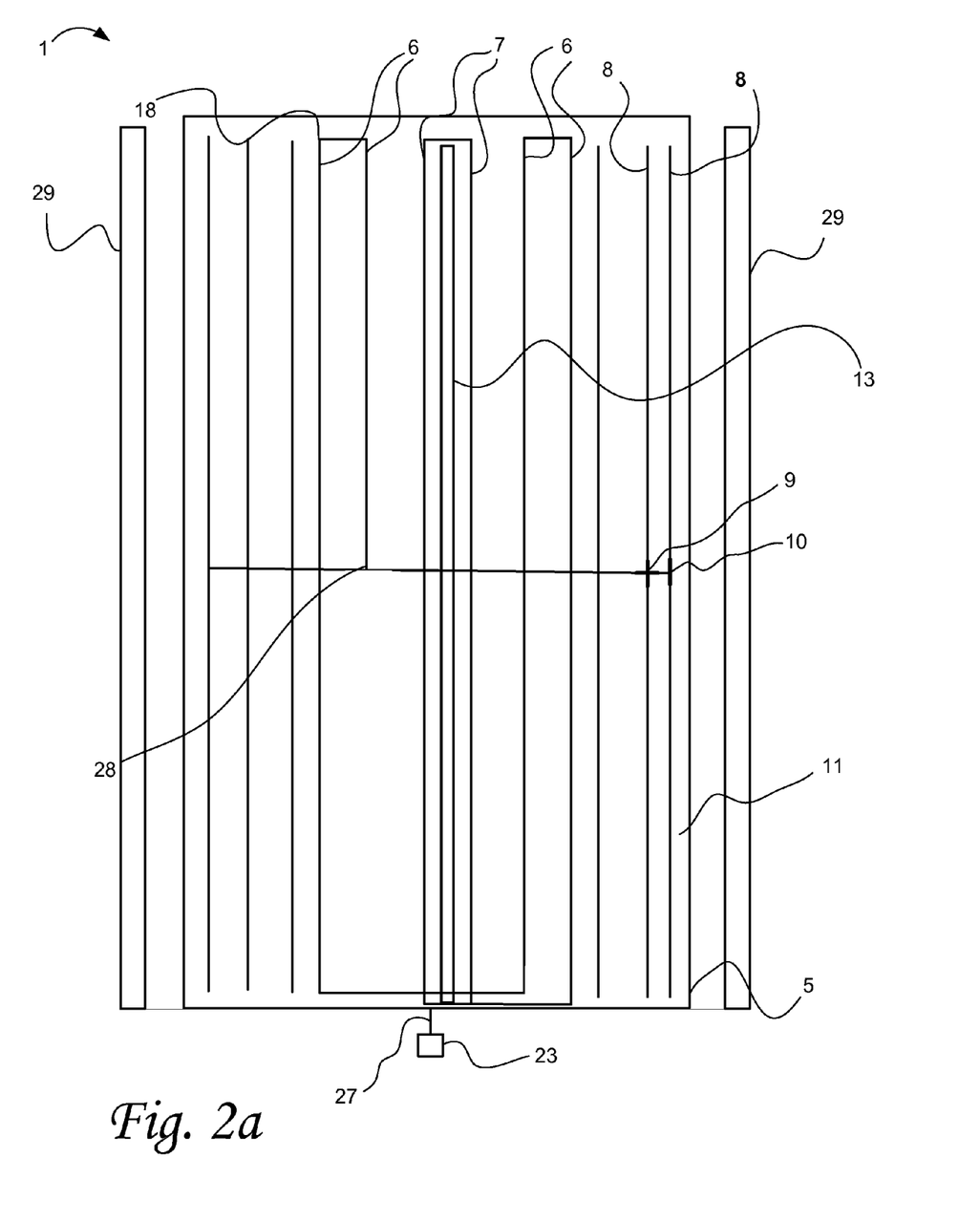
FIG. 2a is a schematic diagram of a top view of a APBR deep pond (partial only)
Figure 2B:
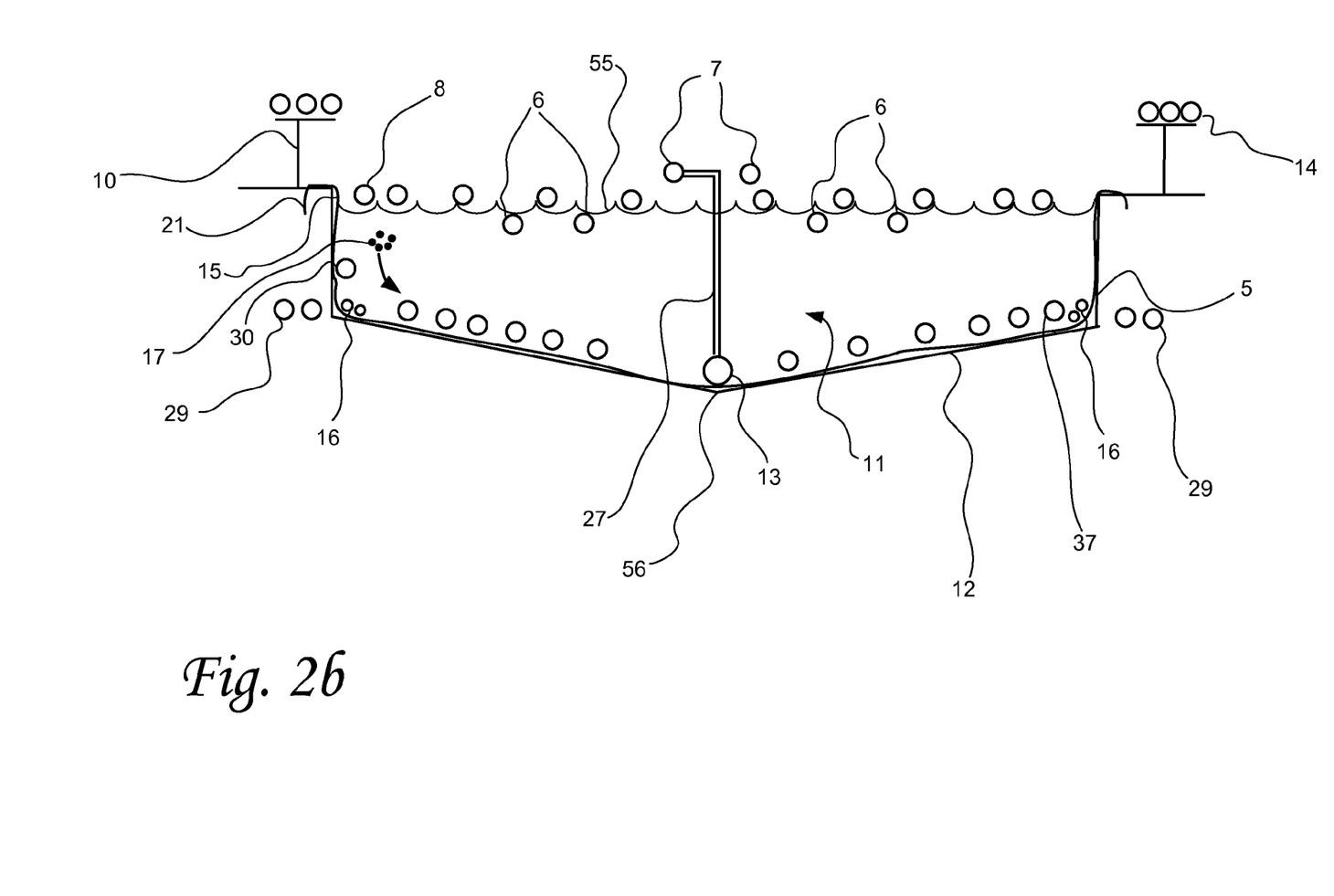
FIG. 2b is a schematic diagram of a front view of a APBR deep pond.

Now referring to FIGS. 2a and 2b, there is provided a schematic diagram of an APBR deep pond illustrating a top view (FIG. 2a) and a front view (FIG. 2b) in accordance with a variant of the present invention. The APBR deep pond 3 comprises of a deep (one foot or deeper) pond 5 with a rectangular shaped perimeter and a bottom 12 having a trough 56 covered with a thick vinyl liner 15. The bottom 12 is sloped from two sides that meet in the interior of the bottom to form the trough 56. In a variant, the cross section of the bottom 12 may resemble a wide v shape.

Figure 3A:
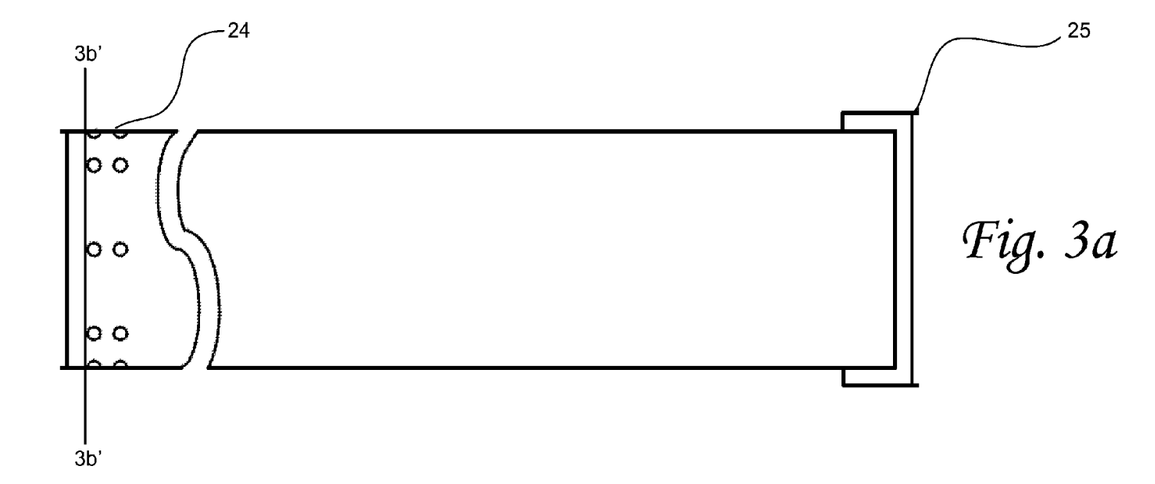
FIG. 3a shows a plan view of the sucking pipe of the APBR deep pond in accordance with one embodiment of the present invention where the pipe is perforated with circular holes.
Figure 3B:
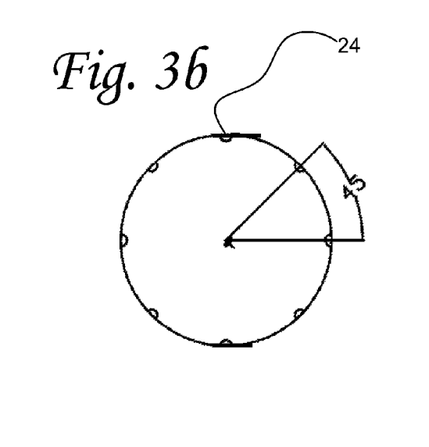
Figure 3C:
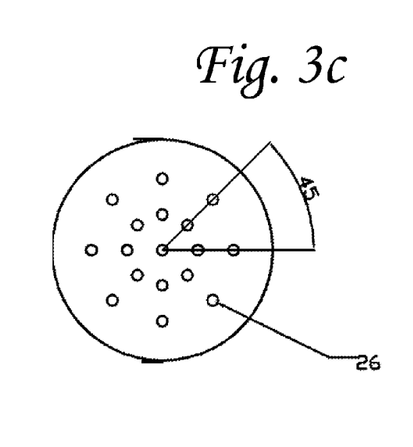
FIG. 3c is a front view of an end cap of the sucking pipe.

The vinyl liner 15 covers the surface of the deep pond 5 on all sides including all edges, which are also covered with dirt at the edges 21. The edges 21 can also be covered with any other appropriate material such as galvanized pipes. At the bottom 22 of the trough 56, there is provided a perforated sucking pipe 13 running along the length of the deep pond 5. One variant of the sucking pipe is illustrated in FIG. 3a, where holes 24 are drilled every 45 degrees apart around the pipe and each set of holes 24 are spaced at every two inches. A cross-sectional view of the sucking pipe taken along the line 3b'-3b' in FIG. 3a is also shown in FIG. 3b, where a hole pattern 31 drilled at every 45 degrees apart is illustrated. At the end of the sucking pipe 13, there is an end cap 25 with holes 26 drilled in a pattern as shown in one embodiment in FIG. 3a. A front view of the end cap 25 is illustrated in FIG. 3c.

Figure 3D:
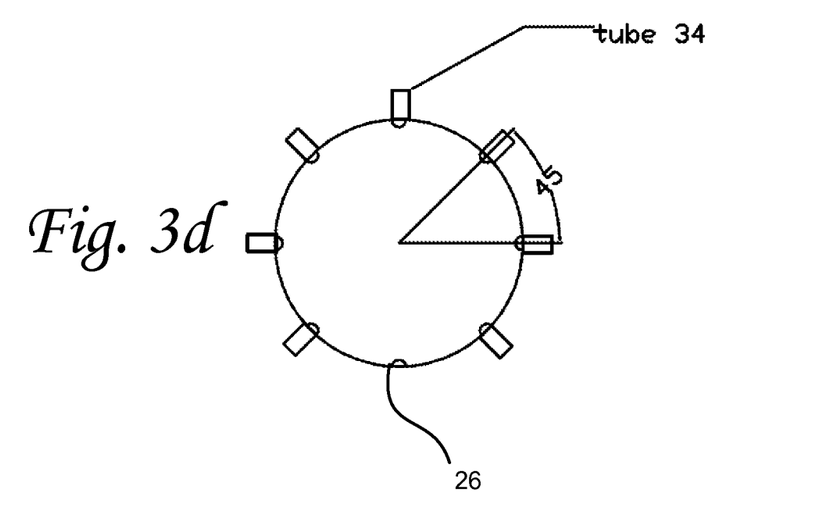
FIG. 3d is a cross section of an alternative embodiment of the sucking pipe where the pipe is protruded with circular pipe nipples.
Figure 3E:
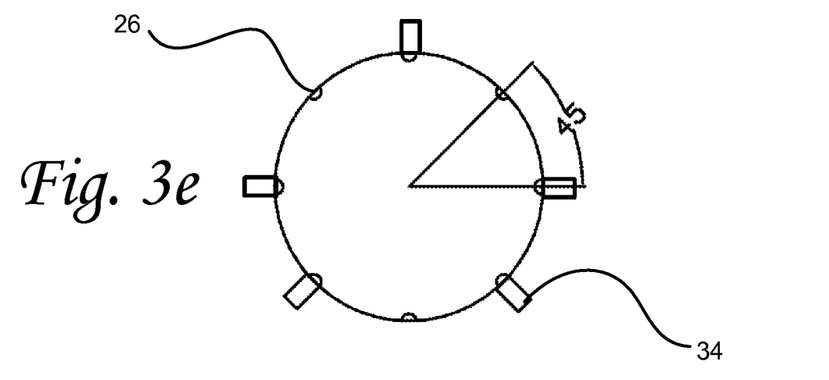
FIG. 3e is cross section of another alternative embodiment of the sucking pipe where the pipe is protruded with circular pipe nipples.
Figure 3F:
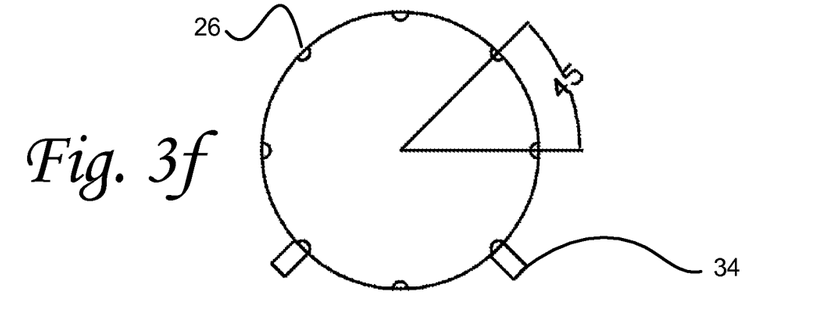
FIG. 3f is a cross section of a further alternative embodiment of the sucking pipe where the pipe is protruded with circular pipe nipples.

Another variant of the sucking pipe 13 is illustrated in FIG. 3d, a cross-sectional view is shown with a pipe nipple 34 protruding from the pipe 13. In certain embodiments, holes 26 and pipe nipples 34 may be mixed as shown in a cross-sectional view in FIG. 3e and a cross-sectional views in FIG. 3f. The size of the sucking pipe 13 and pipe nipple 34 may vary, depending on the size of the pond and the required flow rate.

The lined deep pond 5 is filled with aqueous algae fluid with about 1% microalgae 17 inoculated from the seedling station on a daily basis for a period of time.

The sucking pipe 13 is operated (sucking microalgae from the bottom of the trough 56) via a pump 23 connected through a connection pipe 27. The other side of the pump is connected to a black heating pipe 7 located above the aqueous algae fluid's surface 55. The black heating pipe 7 is of a length that will be adequate to warm microalgae to a desired temperature during cool periods. This black heating pipe 7 is connected to a clear pipe 6, which in one embodiment is located in the aqueous algae fluid's surface 55 (shown in FIG. 2b) and in another embodiment is located above the aqueous algae fluid's surface 55 (not shown), so that the microalgae can be exposed to sunlight. One embodiment of the clear pipe connection is shown in FIG. 2. The length of clear pipe 6 will depend on the desired sunlight exposure time.

The end 28 of clear pipe 6 is connected to a plurality of perforated spray pipes 8 distributed as shown in FIG. 2a in one embodiment of the present invention. The microalgae 17 from the clear pipe 6 are then sprayed out into the air throughout the top surface 55 of the deep pond 5. This allows microalgae 17 a chance to gain exposure to air, $CO_2$, and have exercise for a period of time before falling down and eventually settling down to the bottom of the trough 56 ready for the next cycle of pumping. The perforated spraying pipes 8 may have hole and pipe nipple patterns similar to the sucking pipe discussed earlier. The plurality of perforated spraying pipes 8 are connected together using tees 10 and crosses 9. The perforated spraying pipe 8 may be of different sizes, probably smaller, than the clear pipe 6.

A scenario of a daily operation might start in the morning with the settled down microalgae being pumped through the perforated sucking pipe 13 and passed through the clear pipe 6 at the rate of 6 gallons/minute through a 2 inch diameter pipe (for a 20 cm/sec flow rate). The algae will be exposed to sunlight for about 16 minutes for a 600 ft section of clear pipe, assuming 6 ft of pipe contains about a gallon of algae. If we assume the settling rate for algae is 10 minutes/ft, then each cycle takes one hour for a 6 ft pond. If we further assume that algae has full sunlight exposure during the first half foot of settling time, then the first 5 minutes should be included in the calculation, making the total sunlight exposure time to be 16+5=21 minutes. For an 8 hour/day operation, the algae will be exposed to sunlight for 8×21=168 minutes.

There are at least four approaches in dealing with coldness (in the winter and during cold days and cold nights) and heat. One or more of the following techniques can be employed to solve these situations.

In one approach, a heating rod is used. In one embodiment illustrated in FIG. 2b, heating rods 16 are installed along the surface of the trough edges 21. Since algae are settled around the trough 56 most of the time or during the night, only a small amount of aqueous algae fluid (about 1%) needs to be warmed up in order to keep algae healthy.

A second approach is to install black heating pipes 14 or pads on a supporting rack 20 around the edge of the deep pond 5 and route them to opening holes 28 along side of the pond. Aqueous algae fluid 11 is pumped through these heating black pipes via a pump co-located in the cover of the pump 23 of the perforated sucking pipes 13. These heating pipes can serve a two-fold purpose. They can be used to warm up the aqueous algae fluid in the pond 5 and at the same time serve as sun shading for people.

A third approach is to install black pipes 29 under the ground in order to utilize the constant warm temperature under the ground at the depth of the pond or deeper. Since most algae will be settled to the bottom of the pond most of the time, only aqueous algae fluid in the vicinity needed to be circulated through these pipes in order to keep algae healthy during cold days and cold nights.

A fourth approach is to install black heating pipes 37 for providing heat derived from geothermal sources. The forth approach is to circulate geothermal hot water through pipes 30 located near the bottom of pond. The temperature of geothermal water can vary greatly from $100.^{\circ}F$ to $350.^{\circ}F$ or higher, depending on the location. Hot water can also be generated from an external hot water heater.

Figure 4A:
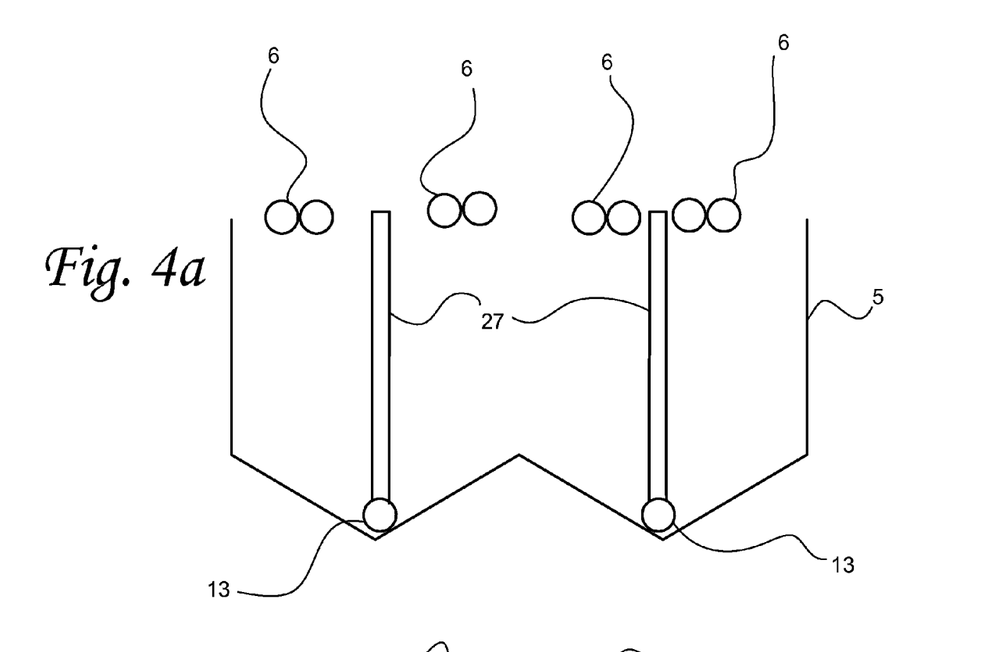
FIG. 4a illustrates an embodiment of a dual-trough bottom pond with dual sets of clear pipes.
Figure 4B:
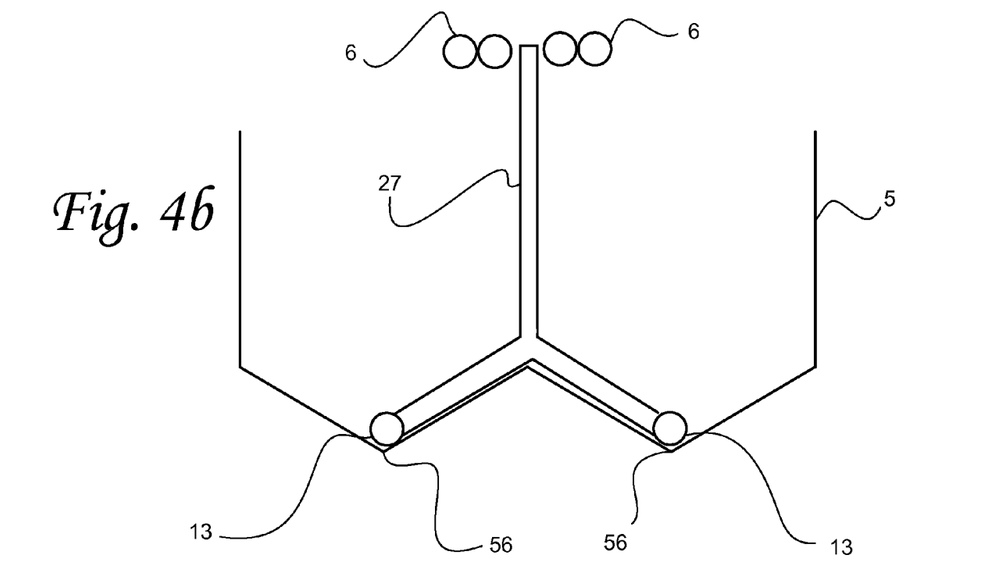
FIG. 4b illustrates an alternative embodiment of a dual-trough bottom pond with a single set of clear pipes.
Figure 4C:
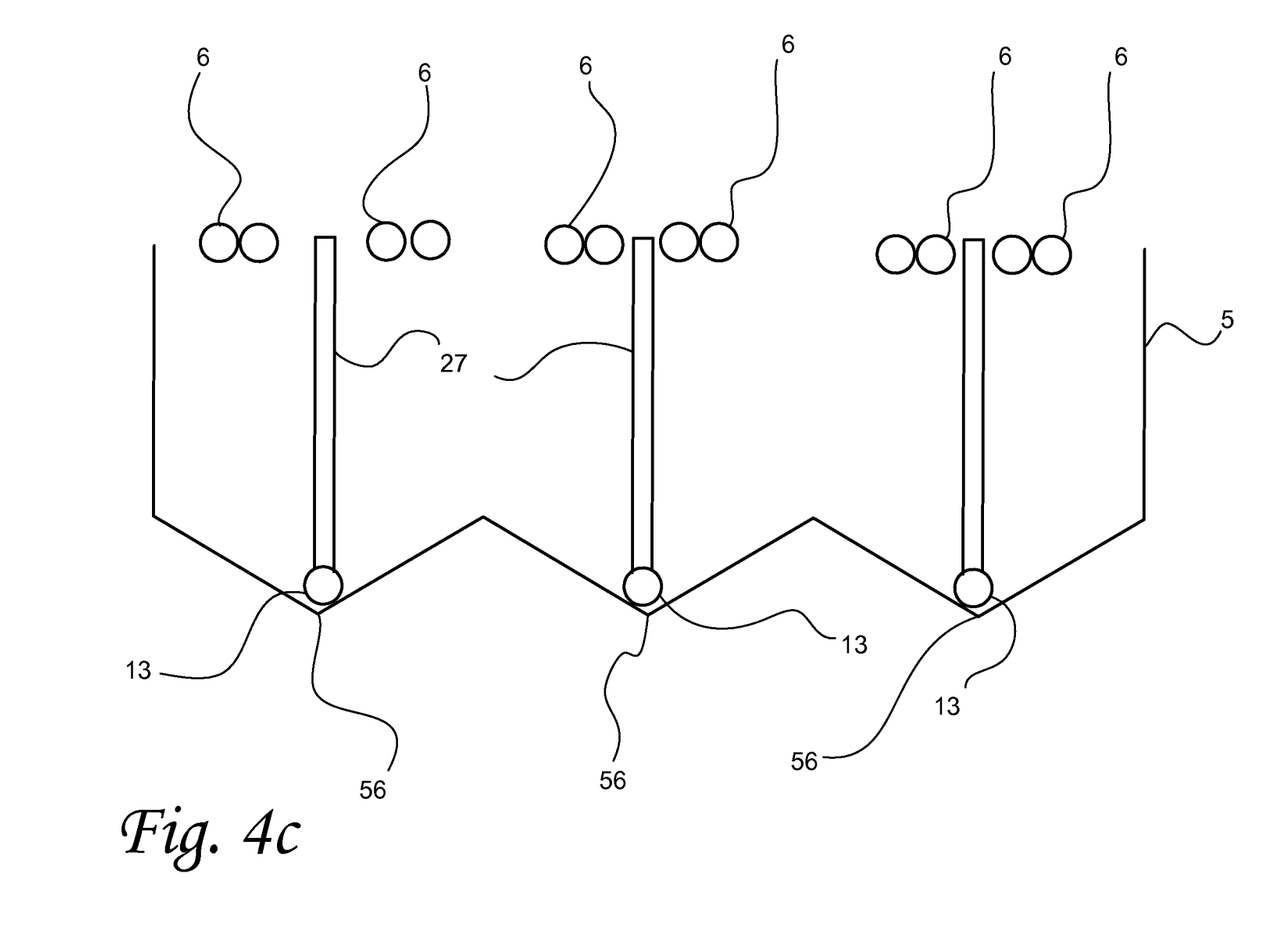
FIG. 4c illustrates an embodiment of a multiple-trough bottom pond with multiple sets of clear pipes.
Figure 4D:
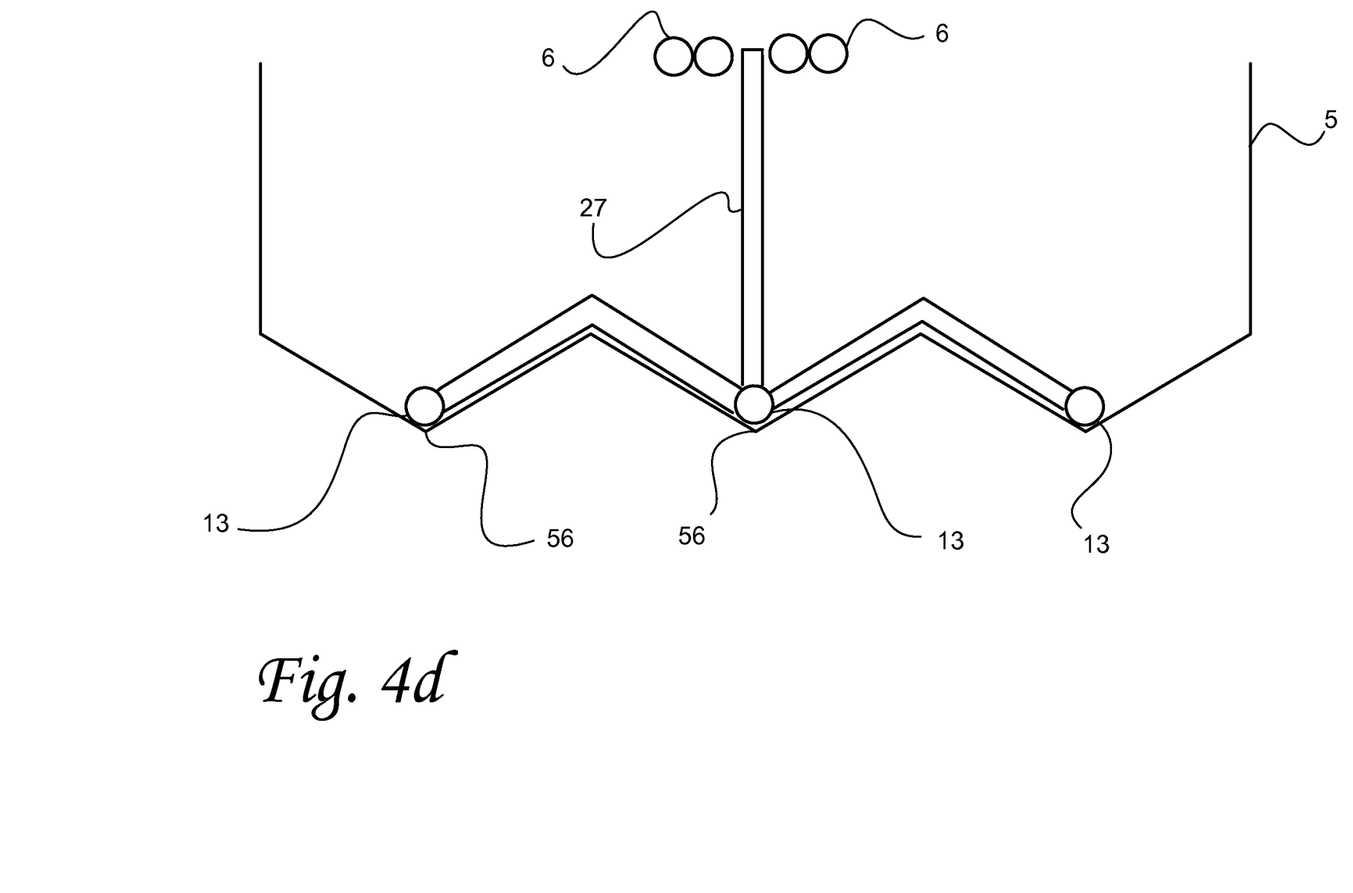
FIG. 4d illustrates an alternative embodiment of a multiple-trough bottom pond with a single set of clear pipes.

Sunlight exposure time can be designed into the APBR deep pond system 1 via the number of troughs 56 provided at the bottom 12 of the deep pond 5. FIGS. 4a and 4b illustrate two embodiments of a dual-trough bottom. Referring to FIG. 4a, in one embodiment, two sets of clear pipes 6 are used to serve the dual troughs, while in another embodiment, referring to FIG. 4b, only one set of clear pipes 6 is used, providing different sunlight exposure times. A multiple-trough bottom 12 is also possible, as depicted in FIGS. 4c and 4d. Again, various sunlight exposure times can be achieved via the number of sets of clear pipes used, which can affect the construction cost.

Figure 5A:
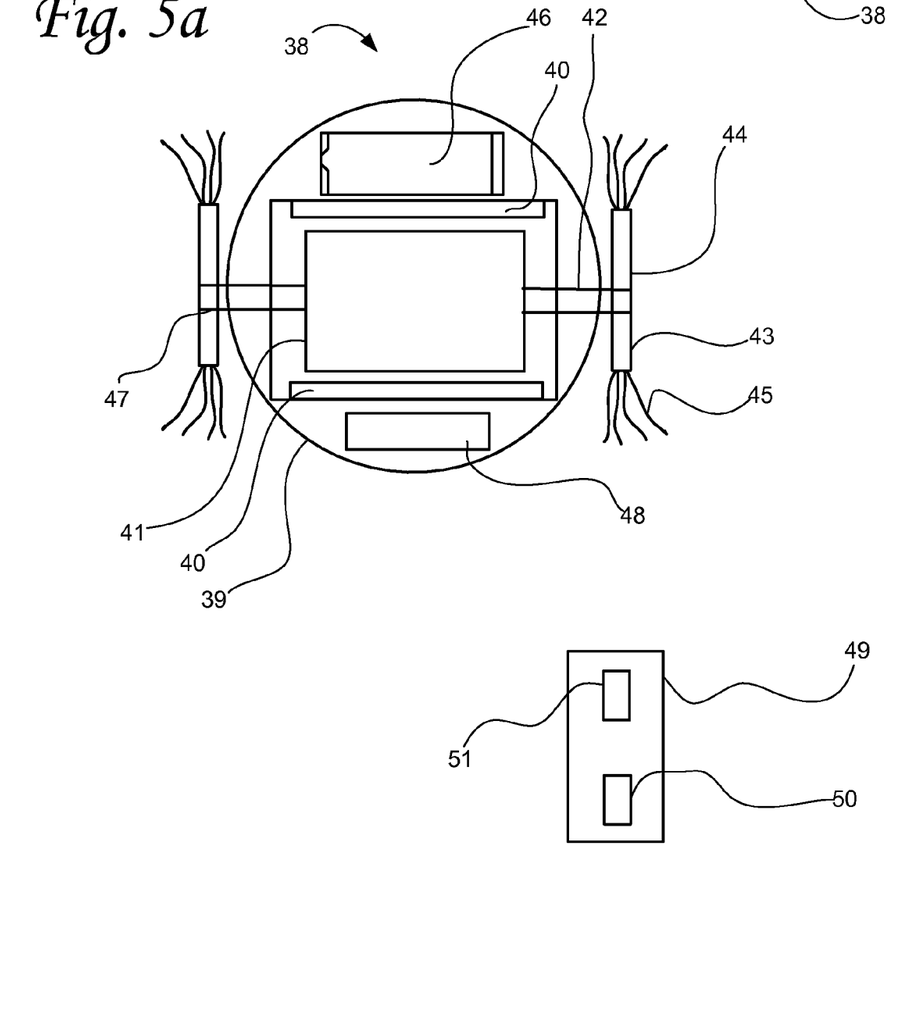
FIG. 5a is a plan view of an embodiment of a Remotely Controlled Electro-Mechanical Scrubbing ball.
Figure 5B:
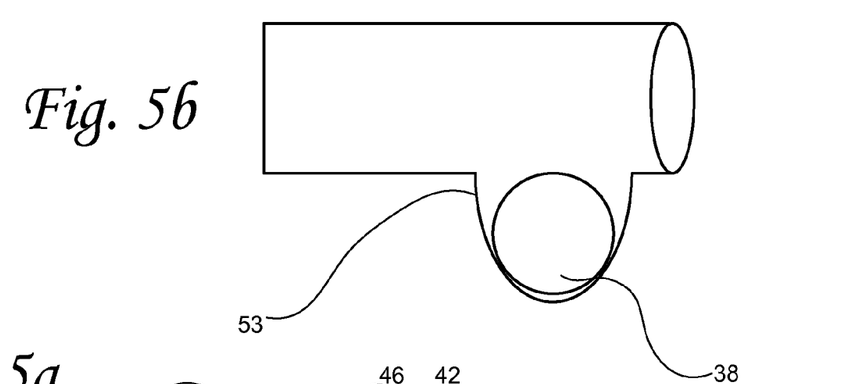
FIG. 5b shows an embodiment of a design of an end pipe pocket for an RCEMS ball.

During operation, algae built up along the interior walls of the pipes 6, 7, 8 may need to be scrubbed. This can be accomplished using various devices such as a sponge ball, a clothe ball, etc. A more effective way is via an electro-mechanical device called the Remotely Controlled Electro-Mechanical Scrubbing (RCEMS) ball 38. One embodiment of this device is shown in FIG. 5a. Each RCEMS ball 38 comprises a rubberized ball 39, an electric motor 40 with an armature 41, having both end shafts 42 protruded through the rubberized ball 39 with a tight seal 47, wherein at the end of each shaft 42, attached a rotor brush 43, consisting of a rotor brush hub 44 and rotor brush hair 45; a rechargeable battery pack 46; a mechanical switch 48 that can be controlled remotely; and a remote control 49 with an on-off switch button 50 and a forward-reverse button 51. Each RCEMS ball will be normally situated in a ball pocket 53 at the end of various pipes in the deep pond as illustrated in FIG. 5b. One embodiment of such locations is at the end of each sucking pipe, each heating pipe, each clear pipe, and each spray pipe.

An example of the operation of a RCEMS ball is as follows: when it is time to scrub the pipe, such as when the aqueous algae fluid is ready for harvest, the ball will be remotely started by an operator pushing the on-off switch button 50 on the remote control 49 (this operation can be programmed to work automatically via a computer). The rotor brushes 43 on the RCEMS ball 38 will start to turn making the ball to start moving. The ball should be moving away from the end of the pipe. But if it moves toward the end of the pipe, its moving direction can be reversed by pushing the forward-reverse button 51.

One advantage of the present invention over other existing practices is that the cultivation volume will be much larger, e.g., 5-12 ft versus 20-50 cm (or 0.66-0.98 ft), i.e., 3 to 18 times.

Another advantage of the present invention is the avoidance or reduction of photo saturation due to the placement of clear pipes near the surface of or submerged under aqueous algae fluid; the vapor of aqueous algae fluid or the large volume of aqueous algae fluid will help to keep the temperature around the plurality of clear pipes at a moderate range during very hot and very cold periods.

Another advantage of the present invention is a longer life resultant of the clear pipes due to moderate temperatures and less exposure to ultraviolet light. Vapor from aqueous algae fluid will help to keep the clear pipes at much lower temperature than the conventional dry-air exposure.

Another advantage of the present invention is the reduction of the amount of clear pipes used. Since only microalgae need to be circulated most of the time, the amount of clear pipes required is smaller, i.e., only about one percent of the aqueous fluid needs to be circulated. In order to circulate the whole volume of aqueous fluid, many sections of clear pipes may be needed.

Another advantage of the present invention is lower construction costs. When less clear pipes are used, less construction cost will be achieved. Also, all pipes whether above or below the aqueous fluid's surface, can be supported partly by the surface of the aqueous fluid, so less supporting structure is needed.

Another advantage of the present invention is that only microalgae need to be circulated most of the time. Since algae will be settled down by gravity and moved toward the pumping pipes located at the center of the trough, they will be sucked up and get circulated. That means only about 1% of aqueous fluid need to be circulated. This will allow more exposure to sunlight to the algae. It has been calculated that the sunlight exposure time of algae in a raceway pond is only about 3 minutes versus about 42 minutes in an APBR system of pipes with about 600 ft in length.

Another advantage of the present invention is that only algae need to be kept warm at night or during cold days. Since algae will be settled down in the trough region, only aqueous fluid in that region needs to be kept warm.

Another advantage of the present invention is the utilization of gravity. Microalgae will settle down toward to bottom of the trough by themselves, so only small amount of energy will be needed to pump them up for recirculation.

Another advantage of the present invention is the reduction of pipes needed to embed underground for ground heat usage. Because algae will be settle down at the trough, only algae need to be circulated through the plurality of pipes underground at night and/or during cold days.

Another advantage of the present invention is the use of solar heating or geothermal heating.

Another advantage of the present invention is that algae will have a resting period during gravity settling time. In the raceway pond, algae will be constantly pushed around the pond. In the APBR pond, algae will be constantly pumped.

Another advantage of the present invention is that the algae will have an exercise and $CO_2$ exposure during the air spray time.

Another advantage of the present invention is the more efficient use of land surface. With the same volume, the efficiency of the land surface area is the ratio of the pond depths. For example, a 5000 cum pond of depth 2 m can use 2 m/0.5 m=4 times less land surface area than a pond of 0.5 m deep (e.g., 10000 sqm vs. 2500 sqm).

Another advantage of the present invention is cheaper construction cost of equipment and infrastructure. To build and install a paddlewheel for a 5000 cum (with 50 m width), a paddle wheel of 24 m (~80 ft) wide could easily cost over $60,000 with support concrete work of another $60,000, while a pumping motor to support this application may cost from only $500 up to $5000.

Another advantage of the present invention is the avoidance of corrosion and seals. When dealing with paddlewheel, we deal with water leaks and corrosion. When deal with pump, all electrical work and motors can be put above ground in a covered area, so minimal work need to be dealt with leaks and corrosion.

Another advantage of the present invention is it can enable the commercial large scale production of microalgae and or microorganisms.

While various embodiments of the present invention have been described above, it should be understood that they have been presented by way of example only, and not of limitation. Likewise, the various diagrams may depict an example architectural or other configuration for the invention, which is done to aid in understanding the features and functionality that can be included in the invention. The invention is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement the desired features of the present invention. Also, a multitude of different constituent module names other than those depicted herein can be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Although the invention is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the invention, whether or not such embodiments are described and whether or not such features are presented as being a part of a described embodiment. Thus the breadth and scope of the present invention should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

A group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise. Furthermore, although items, elements or components of the invention may be described or claimed in the singular, the plural is contemplated to be within the scope thereof unless limitation to the singular is explicitly stated.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether CTRL logic or other components, can be combined in a single package or separately maintained and can further be distributed across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

What is claimed is:

1. An advanced photobioreactor (APBR) deep pond for use to effectively cultivate algae, comprising:
    at least one circulation pump;
    at least one sucking pipe, wherein one end of the sucking pipe is capped off with a perforated cap and another end of the sucking pipe is connected to the circulation pump;
    a plurality of heating pipes for use to warm up aqueous algae fluids, wherein one end of a heating pipe is connected to a circulation pump and another end of the heating pipe is connected to a clear pipe;
    a plurality of clear pipes for exposing aqueous algae fluids to sunlight, wherein one end of the clear pipe is connected to a heating pipe and another end of the clear pipe is connected to a perforated or protruded spraying pipe;
    a plurality of perforated or protruded spraying pipes for use to spray aqueous algae fluids into the air, wherein both ends of the perforated or protruded pipes are capped off;
    wherein the circulation pump is used to pump (circulate) aqueous algae fluids from the sucking pipe into a clear pipe through the heating pipe and spray the aqueous algae fluids out into the air via the plurality of perforated or protruded spraying pipes;
    a plurality of heating elements for warming up aqueous algae fluids;
    a deep pond within which or above which all of the above items are located.

2. The APBR deep pond of claim 1, wherein the pond has a depth of one foot or deeper and having one or more v-shaped troughs in the bottom of the pond.

3. The APBR deep pond of claim 1, wherein the sucking pipes are located at the bottom of each trough.

4. The APBR deep pond of claim 1, wherein the sucking pipes are perforated with holes and/or protruded with pipes of various lengths.

5. The APBR deep pond of claim 1, wherein the heating pipes are located adjacent a top surface of the aqueous algae fluids but not touching the surface, by being disposed on floats.

6. The APBR deep pond of claim 1, wherein the circulation pump is connected on the inlet to the sucking pipe via a vertical pipe and is connected on the outlet to the heating pipe.

7. The APBR deep pond of claim 1, wherein the clear pipes are substantially translucent to sunlight and inhibit the transmission of UV light.

8. The APBR deep pond of claim 1, wherein the clear pipes are submerged on the surface of the aqueous algae fluids with a top of the clear pipe aligned even with or below the surface of the aqueous algae fluids.

9. The APBR deep pond of claim 1 further comprising a gas relief valve, located above and beyond the surface of the aqueous algae fluids, and is connected to the clear pipe.

10. The APBR deep pond of claim 1 further comprising a $CO_2$ or Flue Gas Desulphurization (FGD) $CO_2$ injector connected to the clear pipe.

11. The APBR deep pond of claim 10, wherein the $CO_2$ or FGD $CO_2$ injector is a venturi-type injector.

12. The APBR deep pond of claim 10, wherein the $CO_2$ or FGD $CO_2$ injector is located above the surface of the aqueous algae fluids with a pipe extending down into the aqueous algae fluid down the bottom of the deep pond.

13. The APBR deep pond of claim 1, wherein the heating elements are located at the bottom of the deep pond and above the surface of the trough and run parallel with the sucking pipe.

14. The APBR deep pond of claim 1, wherein the circulation pipes of the hot water draw the hot water from geothermal wells and the hot water pipes are located at the side and/or bottom of the pond.

15. A method of cultivating algae, comprising:
growing a species of algae in the APBR deep pond of claim 1.

16. The APBR deep pond of claim 1, further comprising a remotely controlled electro-mechanical scrubbing (RCEMS) ball for cleaning pipes.

17. The RCEMS ball of claim 16, further comprising:
an armature having first and second ends;
a remote control and a rubberized ball, which contains a rechargeable battery pack;
an electromechanical switch that can be turned on and off remotely; and
an electric motor with both ends of the armature exposed outside, but sealed, with a round brush attached on each end.

18. The APBR deep pond of claim 17, wherein a pocket is disposed at the ends of any of the one or more pipes configured to house the RCEMS ball during the non-operative period.

19. An advanced photobioreactor (APBR) deep pond system for use to
effectively cultivate algae, comprising:
a seedling station for conditioning the aqueous fluids to be cultivated; a harvesting station for receiving the aqueous fluids being cultivated, and
an advanced photobioreactor (APBR) deep pond for use to cultivate microalgae, where the APBR deep pond comprises:
one or more perforated or protruded sucking pipes, wherein one end of the pipe is capped off with a perforated cap and the other end is connected to an electric pump;
a plurality of heating pipes for use to warming up aqueous algae fluids, wherein one end is connected to a pump and the other end is connected to a clear pipe;
a plurality of clear pipes for exposing aqueous algae fluids to sunlight, wherein one end of the pipe is connected to a heating pipe and the other end is connected to a perforated or protruded spraying pipe;
a plurality of perforated or protruded spraying pipes for use to spray aqueous algae fluids into the air, wherein both ends are capped off;
one or more electric pumps for pumping (circulating) aqueous algae fluids from the sucking pipe into a clear pipe through the heating pipe and spraying the aqueous algae fluids out into the air via a plurality of perforated or protruded spraying pipes;
a plurality of heating rods for use to warm up aqueous algae fluids;
a second plurality of heating pipes for use to warm up aqueous algae fluids to be located on supporting brackets situated around sides of the pond above ground;

one or more second pumps for circulating aqueous algae fluids; a plurality of pipes for use to warm up aqueous algae fluids;

a plurality of pipes for circulating hot water from geothermal wells in order to warm up aqueous algae fluids;

and a liner covered deep pond within which or above which all of the above items are located.

20. A method of cultivating algae comprising cultivating the algae in the APBR deep pond of claim 19.

* * * * *